United States Patent
Bergman et al.

(10) Patent No.: US 12,312,709 B2
(45) Date of Patent: May 27, 2025

(54) COMPOSITION, METHOD, AND APPARATUS FOR FABRICATING SILK PROTEINS AND PRODUCTS THEREOF

(71) Applicants: Haley Bergman, Davis, CA (US);
Preston Vanderpan, Davis, CA (US);
Avery Williamson, Davis, CA (US)

(72) Inventors: Haley Bergman, Davis, CA (US);
Preston Vanderpan, Davis, CA (US);
Avery Williamson, Davis, CA (US)

(*) Notice: Subject to any disclaimer, the term of this patent is extended or adjusted under 35 U.S.C. 154(b) by 402 days.

(21) Appl. No.: 17/805,012

(22) Filed: Jun. 1, 2022

(65) Prior Publication Data
US 2022/0380942 A1 Dec. 1, 2022

Related U.S. Application Data

(60) Provisional application No. 63/195,362, filed on Jun. 1, 2021.

(51) Int. Cl.
*D01F 4/02* (2006.01)
*C07K 14/435* (2006.01)
*C08J 5/18* (2006.01)

(52) U.S. Cl.
CPC .......... *D01F 4/02* (2013.01); *C07K 14/43563* (2013.01); *C08J 5/18* (2013.01)

(58) Field of Classification Search
CPC ........ C07K 14/43586; C07K 14/43536; C07K 1/145; C07K 1/34; C07K 14/43563; C07K 14/43518; C08J 5/18; C08J 2201/0444; C08J 2201/0504; C08J 2205/022; C08J 2389/00; C08J 3/07; C08J 3/075; C08J 9/0061; C08J 9/26; C08J 9/28; C08L 89/00; B29C 39/003; B29C 39/203; B29C 55/005; B29C 64/106; B29C 64/209; D01D 5/0007; D01D 1/02; D01D 5/16; A23J 1/00; A23J 3/04; B01D 1/14; B01D 1/16; B01D 1/18; B01D 11/0211; B01D 11/0257; B01D 11/0261; B01D 11/028; B01D 2315/10; B01D 2315/16; B01D 37/048; B01D 61/14; B01D 61/146; B01D 61/147;
(Continued)

(56) References Cited

U.S. PATENT DOCUMENTS

2016/0318247 A1* 11/2016 Schlachter ............ B29C 64/106
2019/0084223 A1* 3/2019 Wilenski ............... B29C 64/314
(Continued)

*Primary Examiner* — Seyed Masoud Malekzadeh
*Assistant Examiner* — Tiffany Yu Huang
(74) *Attorney, Agent, or Firm* — Osha Bergman Watanal

(57) ABSTRACT

A method of producing a fibroin protein product includes providing a stock solution of fibroin protein, injecting a first injection solution including a chaotropic salt into the stock solution, injecting a second injection solution including a kosmotropic salt into the stock solution to provide an intermediate solution, and exposing the intermediate solution to a shear force. A method of preparing a stock solution of fibroin protein includes dissolving a silk fiber into a protic solvent to provide a solution including fibroin protein and adding a chaotropic salt to the solution including fibroin protein to provide the stock solution of fibroin protein. A 3D printer includes a first extruder, a closed duct assembly, at least one injection site, a filter assembly, a printer head assembly, and a printer body.

7 Claims, 8 Drawing Sheets

(58) Field of Classification Search
CPC .... B01D 61/22; B01D 63/10; D10B 2211/04; D10B 2211/22
See application file for complete search history.

(56) References Cited

U.S. PATENT DOCUMENTS

2022/0235099 A1* 7/2022 Kamikubo ............. D01D 11/00
2022/0372665 A1* 11/2022 Baryshyan ............... B01D 1/16

* cited by examiner

COMPOSITION, METHOD, AND APPARATUS FOR FABRICATING SILK PROTEINS AND PRODUCTS THEREOF

BACKGROUND

Various synthetic and biologically derived materials exist for use in human tissue construction and repair. In particular, musculoskeletal treatments often rely on grafts of natural or synthetic materials. While synthetic materials, such as hard plastics and glass, are non-toxic and non-immunogenic, they are incapable of supporting necessary cellular activity and often pose a severe risk when integrated with native tissue. On the other hand, natural material grafts often require multiple procedures, incorporate slowly into native tissue, and lose their original mechanical properties. Therefore, the development of inexpensive biomaterials that are capable of supporting cellular and mechanical activity has been a long-standing goal in the biomedical scientific community.

Silk produced from insects and arachnids, such as spiders and silkworms, has recently received attention as a promising biomaterial for use in tissue construction and repair, as it is biocompatible and has immense tensile strength. Unfortunately, manufactured silk typically has poor mechanical properties, low reproducibility, and relies on expensive lab equipment and caustic chemical reagents for the artificial spinning systems used for its preparation. The lack of parametric control in the core processes of native silk production restricts the preparation of affordable, high-quality artificial silk on an industrial scale.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a 3D printer including a first extruder coupled to a chemical gradient line and a closed duct assembly coupled to the chemical gradient line downstream of the first extruder. At least one injection site is coupled to the chemical gradient line downstream of the closed duct assembly. A first injection site of the at least one injection site is coupled to a second extruder. A filter assembly is coupled to the chemical gradient line downstream of the at least one injection site. A third extruder is coupled to the chemical gradient line through a first port in the filter assembly, and a collection syringe is coupled to the chemical gradient line through a second port in the filter assembly. A printer head assembly is coupled to the chemical gradient line downstream of the filter assembly. Finally, the 3D printer includes a printer body that has a microprocessing system.

In another aspect, embodiments disclosed herein relate to a method of producing a fibroin protein product that includes providing a stock solution of fibroin protein, injecting a first injection solution comprising a chaotropic salt into the stock solution, injecting a second injection solution comprising a kosmotropic salt into the stock solution to provide an intermediate solution, and exposing the intermediate solution to a shear force.

In yet another aspect, embodiments disclosed herein relate to a method of preparing a stock solution of fibroin protein that includes dissolving a silk fiber into a protic solvent to provide a solution comprising fibroin protein and adding a chaotropic salt to the solution comprising fibroin protein to provide the stock solution of fibroin protein.

Other aspects and advantages of the claimed subject matter will be apparent from the following description and the appended claims.

DETAILED DESCRIPTION

Figure 1:
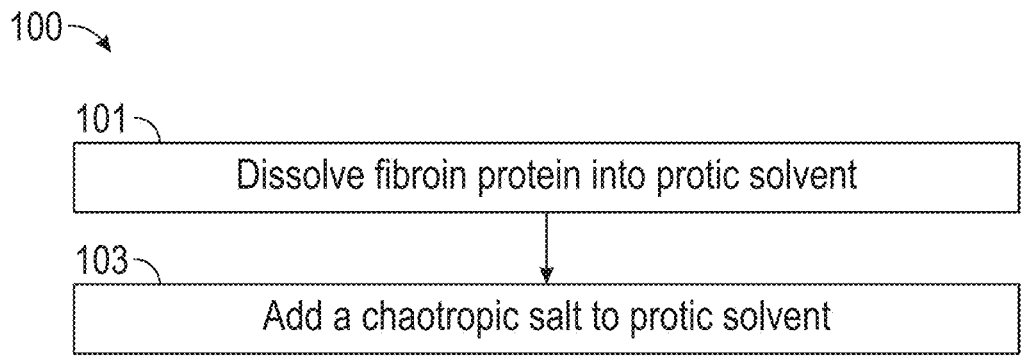
FIG. 1 is a block flow diagram of a method of making a solution of fibroin proteins in accordance with one or more embodiments of the present disclosure.

The present disclosure generally relates to compositions of fibroin protein solutions and preparations and uses thereof. Fibroin protein solutions may include fibroin protein that is stable at ambient conditions. Methods to prepare such solutions may include an decreasing pressure gradient. One or more embodiments relate to the use of fibroin protein solutions in the preparation of fibroin protein products. Various types of fibroin protein products may be produced using compositions and methods according to the present disclosure. Particular embodiments may relate to 3D printing fibroin protein products. Such embodiments may include a printer specifically designed to print fibroin protein products disclosed herein.

Fibroin Protein Solution

In one aspect, embodiments disclosed herein relate to a fibroin protein solution composition and methods of preparation thereof. Fibroin protein solutions may include one or more fibroin proteins. Fibroin protein solutions described herein may provide fibroin protein that is stable at ambient conditions. For example, disclosed fibroin protein solutions may be stable for at least 1 week at temperatures ranging from 4 to 40° C. Such fibroin protein solutions may be stable under a moderate amount of shear stress, such as shear stress experienced by shaking, swirling, or dropping the fibroin protein solution. Disclosed fibroin protein solutions may include an aqueous-based fluid, at least one fibroin protein, and one or more kosmotropic and chaotropic ions. Used throughout the description, the fibroin protein solution may be referred to as the stock solution.

In one or more embodiments, the fibroin protein solution includes an aqueous-based fluid. The aqueous-based fluid includes water. The water may be distilled water, deionized water, milli-q water, or combinations thereof. Water may be included in the aqueous-based fluid in an amount ranging from 15 to 85 wt % (weight percent), based on the total weight of the aqueous-based fluid. For example, in one or more embodiments, water may be included in the aqueous-based fluid of a fibroin protein solution in an amount ranging from a lower limit of one of 15, 20, 25, 30, 35, and 40 wt % to an upper limit of one of 60, 65, 70, 75, 80, and 85 wt %, where any lower limit may be paired with any mathematically compatible upper limit.

In one or more embodiments, the aqueous-based fluid includes an alcohol. Suitable alcohols that may be included in an aqueous-based fluid of disclosed compositions include methanol, ethanol, propanol, isopropanol, butanol, isobutanol, and pentanol, among others. In one or more particular embodiments, the aqueous-based fluid includes ethanol.

The aqueous based fluid may include an alcohol in an amount ranging from 15 to 85 wt %, based on the total weight of the aqueous-based fluid. For example, an alcohol may be included in the aqueous-based fluid in an amount ranging from a lower limit of one of 15, 20, 25, 30, 35, and 40 wt % to an upper limit of one of 60, 65, 70, 75, 80, and 85 wt %, where any lower limit may be paired with any mathematically compatible upper limit.

In one or more embodiments, the aqueous-based fluid includes at least one chloride salt. For example, the aqueous-based fluid may include one or more of sodium chloride, calcium chloride, magnesium chloride, ammonium chloride, among others. In such embodiments, the salt may be included in an amount ranging from 0.05 to 5.0 wt %, based on the total weight of the aqueous-based fluid. In some embodiments, a salt may be added to the aqueous-based fluid in an amount ranging from a lower limit of one of 0.05, 0.1, 0.2, 0.5, and 1.0 wt % to an upper limit of one of 1.0, 2.0, 3.0, 4.0, and 5.0 wt %, where any lower limit may be paired with any mathematically compatible upper limit.

In one or more embodiments, the aqueous-based fluid includes water, an alcohol, and a salt. In one or more particular embodiments, the aqueous-based fluid is Ajisawa's reagent.

In one or more embodiments, the fibroin protein solution composition includes at least one fibroin protein. Fibroin is a protein found in silk produced by various silk-producing genera such as insects and arachnids. The C-terminal and N-terminal domains of fibroin are conserved among all silk-producing genera, allowing for the use of fibroin proteins from various sources in the disclosed compositions. Suitable fibroin proteins may include, but are not limited to, natural proteins produced by spiders such as the *Nephila clavipes*, and silkworms such as the *Bombyx mori*; synthetic proteins engineered from yeast, bacteria, and goats; recombinant proteins; and combinations thereof. For example, in one or more embodiments, the fibroin protein included in a fibroin protein solution is a purified spidroin protein, a purified silkworm fibroin protein, a native spider silk web, an engineered fibroin protein from yeast, an engineered protein from bacteria, an engineered protein from goats, or a combination thereof. In other embodiments, fibroin proteins may be recombinant proteins prepared from a one or more natural or synthetic protein, provided that the resulting recombinant protein has the conserved N-terminal and C-terminal domains.

Fibroin protein solutions in accordance with the present disclosure may include fibroin protein in an amount ranging from 0.5 to 50% w/v (percent weight by volume). For example, in one or more embodiments, fibroin protein is included in a fibroin protein solution in an amount ranging from a lower limit of one of 0.5, 1.0, 2.0, 5.0, 10 and 15% w/v to an upper limit of one of 20, 25, 30, 35, 40, 45, and 50% w/v, where any lower limit may be paired with any mathematically compatible upper limit.

In one or more embodiments, fibroin protein solution compositions include a chaotropic salt. Chaotropic salts interfere with water-water interactions, effectively disrupting water structure and denaturing any proteins in the water. As such, inclusion of a chaotropic salt in the fibroin protein solution may prevent early aggregation of the fibroin protein. Suitable chaotropic salts that may be included in fibroin protein solutions include, but are not limited to, $Na_2SO_4$, $(NH_4)_2SO_4$ $CaCl_2$, $MgCl_2$, NaCl, NaBr, NaI, and combinations thereof. In particular embodiments, compositions include NaCl.

Fibroin protein solutions may include the chaotropic salt in a concentration ranging from 130 to 170 mM. For example, compositions of the present disclosure may include at least one chaotropic ion in a concentration ranging from a lower limit of one of 130, 135, 140, 145, and 150 mM to an upper limit of one of 150, 155, 160, 165, and 170 mM, where any lower limit may be paired with any mathematically compatible upper limit. The concentration of the at least one chaotropic salt may be selected so as to correspond to the concentration of the same chaotropic salt in a native silk-producing gland of an insect.

In some embodiments, more than one chaotropic salt is included in the fibroin protein solution. Suitable chaotropic salts are as previously described. Compositions including more than one chaotropic salts may include NaCl as a first chaotropic salt and $(NH_4)_2SO_4$ as a second chaotropic salt. In such embodiments, the first chaotropic salt may be included in a concentration ranging from 130 to 170 mM, as above, and the second chaotropic salt may be included in a concentration ranging from 500 to 1500 mM. For example, fibroin protein solutions including more than one chaotropic salts may include the second chaotropic salt in a concentration ranging from a lower limit of one of 500, 600, 700, 800, 900, and 1000 mM to an upper limit of one of 1000, 1100, 1200, 1300, 1400, and 1500 mM, where any lower limit may be paired with any mathematically compatible upper limit.

In one or more embodiments, compositions optionally include a chemical chaperone. A chemical chaperone may be included in compositions of the present disclosure to stabilize the fibroin protein in the solution and reduce the amount of premature protein folding that may otherwise occur. Suitable chemical chaperones that may be included in fibroin protein solutions include, but are not limited to, urea, glycerol, trehalose, trimethylamine n-oxide, glycine, and combinations thereof. In particular embodiments, urea is added to the fibroin protein solution as a chemical chaperone.

In one or more embodiments, fibroin protein solution compositions may have a pH that corresponds to a pH in a native silk-producing gland of a silk-producing genera. The pH may be suitable for the fibroin protein to be stable in solution at ambient conditions. Such pH may be neutral to basic. For example, compositions may have a pH ranging from 4.0 to 12.0. One or more fibroin protein solutions of the present disclosure have a pH ranging from a lower limit of one of 4.0, 4.5, 5.0, 5.5, 6.0, 6.5, 7.0, and 7.5 to an upper limit of one of 8.0, 8.5, 9.0, 9.5, 10.0, 10.5, 11.0, 11.5, and 12.0, where any lower limit may be paired with any mathematically compatible upper limit.

In one or more embodiments, fibroin protein solutions may exhibit high stability at ambient conditions. As mentioned above, fibroin protein solutions in accordance with the present disclosure may be stable for at least 1 week at temperatures ranging from 4 to 40° C. In some embodiments, fibroin protein solutions may be stable at a temperature ranging from a lower limit of one of 4, 5, 8, 10, 15, and 20° C. to an upper limit of one of 25, 30, 35, and 40° C., where any lower limit may be paired with any mathematically compatible upper limit. Similarly, fibroin protein included in compositions disclosed herein may have enhance stability to moderate shear stress, compared to fibroin protein in solutions made according to conventional methods. Such stability may allow for the preparation of fibroin protein solutions having a high concentration of fibroin protein (e.g., 50% w/v).

Method of Preparing a Fibroin Protein Solution

As described above, fibroin protein solutions of the present disclosure may be prepared to provide fibroin protein that is stable in solution at ambient conditions. In the disclosed method, the components may be introduced in a manner that corresponds to an environment of a native silk-producing gland of an insect.

Method 100 of preparing a fibroin protein solution in accordance with one or more embodiments is depicted in FIG. 1. Initially, method 100 includes dissolving fibroin protein into a protic solvent 101. In some embodiments, the protic solvent is an aqueous-based fluid as previously described. In other embodiments, the protic solvent is an alcohol. In such embodiments, the alcohol may include at least one chloride salt as previously described. The fibroin protein may be any suitable purified fibroin protein.

In one or more embodiments, the fibroin protein is added to the protic solvent such that the protic solvent includes the fibroin protein in a concentration ranging from 0.5 to 50% w/v. For example, in one or more embodiments, the fibroin protein may be dissolved in the protic solvent in an amount ranging from a lower limit of one of 0.5, 1.0, 2.0, 5.0, 10 and 15% w/v to an upper limit of one of 20, 25, 30, 35, 40, 45, and 50% w/v, where any lower limit may be paired with any mathematically compatible upper limit In particular embodiments, the protic solvent includes the fibroin protein in a concentration of about 50% w/v.

In order to achieve dissolution of the fibroin protein, once the fibroin protein has been added to the protic solvent, the solution may be stirred at an elevated temperature for a suitable amount of time. In one or more embodiments, the protic solvent including the fibroin protein may be stirred at 200 to 300 rpm, for 2.0 to 5.0 hours. For example, stirring may be carried out at a speed ranging from a lower limit of any of 200, 215, 230, 245, and 250 rpm, to and upper limit of any of 250, 265, 275, 290, and 300 rpm, where any lower limit may be paired with any mathematically compatible upper limit, for an amount of time ranging from a lower limit of one of 2.0, 2.5, 3.0, and 3.5 hours to an upper limit of one of 3.5, 4.0, 4.5, and 5.0 hours, where any lower limit may be paired with any mathematically compatible upper limit.

As mentioned above, the fibroin protein may be dissolved in the protic solvent at an elevated temperature. Any suitable elevated temperature may be used, provided that it is sufficient to dissolve the fibroin protein into the protic solvent but does not denature the fibroin protein. In one or more embodiments, the dissolution of the fibroin protein may be carried out at an elevated temperature ranging from 50 to 120° C. For example, the fibroin protein may be dissolved in the protic solvent at an elevated temperature ranging from a lower limit of one of 50, 55, 60, 65, 70, 75, 80, and 85° C. to an upper limit of one or 90, 95, 100, 105, 110, 115, and 120° C., where any lower limit may be paired with any mathematically compatible upper limit.

After the fibroin protein is dissolved in the protic solvent, a chaotropic salt may be added to the protic solvent fluid 103. The chaotropic salt is as previously described. In one or more embodiments, more than one chaotropic salts are added to the aqueous-based fluid. In some such embodiments, a first chaotropic salt and a second chaotropic salt are added together. In other embodiments, they are added separately.

In method 100, the chaotropic salt may be added to the protic solvent such that the resulting solution has a specific concentration the chaotropic salt as previously described. The final concentration of the chaotropic salt may correspond to the concentration of the same in a native silk-producing gland of a silk-producing genera. In embodiments in which more than one chaotropic salts are added to the protic solvent, the final concentration of each chaotropic salt may correspond to the concentration of the same in a native silk-producing gland. The final concentration of each of the chaotropic salts is as previously described.

While the chaotropic salt may be added as a salt directly to the protic solvent, as will be appreciated by those skilled in the art, solutions including the chaotropic salt may be prepared separately and then added to the aqueous base fluid. Such solutions may include water.

Method 100 optionally includes adding a chemical chaperone to the protic solvent in order to provide a fibroin protein solution of one or more embodiments. Addition of a chemical chaperone may help to limit any premature folding of the fibroin protein. The identity and amount of optional chemical chaperone is as previously described. As described above, method 100 includes dissolving a purified fibroin protein is into an protic solvent 101. However, in one or more embodiments, methods initially include purifying a native source of fibroin protein such as a spider silk web. Such purification of a native source of fibroin protein may be carried out according to methods known in the art. For example, in a particular embodiment, a spider silk web may first be cleaned to remove debris. Then, the cleaned web may be degummed to remove the tightly bound shell layer and provide pure fibroin protein.

Method of Producing Fibroin Protein Products

In another aspect, the present disclosure relates to methods of producing fibroin protein products using previously described fibroin protein solutions. One or more embodiment methods may include subjecting a fibroin protein solution to an decreasing pressure gradient to provide fibroin protein products.

Figure 2:
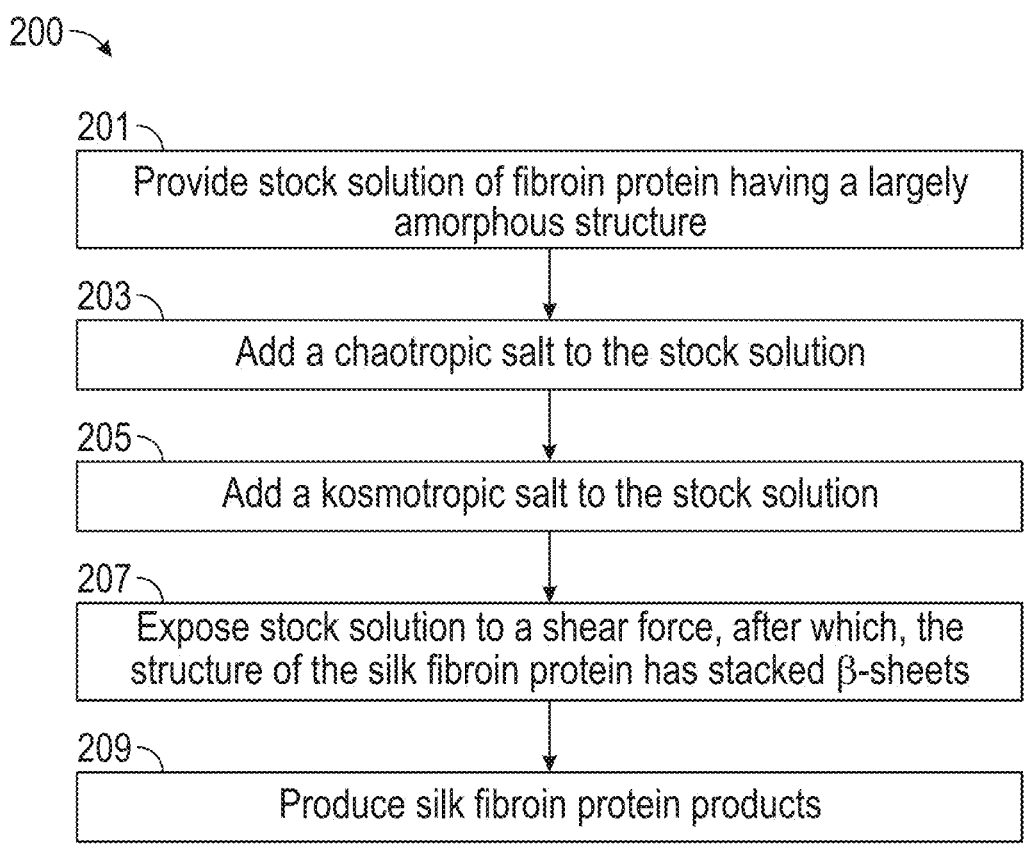
FIG. 2 is a block flow diagram of a method of producing a fibroin protein product in accordance with one or more embodiments of the present disclosure.

An exemplary method, 200, of producing silk fibroin products is provided in, and discussed with reference to, FIG. 2. First, method 200 includes providing a stock solution including fibroin protein 201. The stock solution may be a fibroin protein solution as previously described. The fibroin protein in the stock solution may have a structure that is largely amorphous, with a small amount of embedded β-sheets. In the stock solution, the β-sheets are limited from self-aligning to form a structure with stacked β-sheets having an increased degree of crystallinity due to additional components that stabilize a denatured structure.

Method 200 then includes adding a first injection solution including a chaotropic salt to the stock solution 203, followed by a second injection solution including a kosmotropic salt to provide an intermediate solution 205. Injection of the kosmotropic salts may induce aggregation and acidification of the fibroin protein solution.

Suitable chaotropic and kosmotropic salts that may be added to the stock solution include, but are not limited to, $NaHCO_3$, $Na_2CO_3$, $Cs_2CO_3$, NaCl, $K_2CO_3$ KCl, KI, $Na_2SO_4$, $KH_2PO_4$, $NaH_2PO_4$, $NaC_6H_7O_7$, $Na_2C_6H_6O_7$, $K_3C_6H_5O_7$, KBr, $(NH_4)_2SO_4$, and combinations thereof. In particular embodiments, the chaotropic salt is $NaHCO_3$/$Na_2CO_3$ and the kosmotropic salt is $KH_2PO_4$.

In one or more embodiments, the chaotropic salt and the kosmotropic salt are added to the stock solution in an amount such that the concentration of each salt in the intermediate solution corresponds to the concentration of the same in a native silk-producing gland. For example, the chaotropic salt may be included in the intermediate solution in a concentration ranging from 0 to 50 mM. In one or more embodiments, the chaotropic salt may be included in the intermediate solution in a concentration ranging from a lower limit of one of 0, 1, 2, 5, 10, 15, and 20 mM to an upper limit of one of 20, 25, 30, 35, 40, 45, and 50 mM, where any lower limit may be paired with any mathematically compatible upper limit. The kosmotropic salt may be included in the intermediate solution in a concentration ranging from 0.1 to 1.0 M (molar). For example, in one or more embodiments, the intermediate solution includes the kosmotropic salt in a concentration ranging from a lower limit of one of 0.1, 0.2, 0.3, 0.4, and 0.5 M, to an upper limit of one of 0.5, 0.6, 0.7, 0.8, 0.9, and 1.0 M, where any lower limit may be paired with any mathematically compatible upper limit.

As previously described, the addition of a chaotropic salt and a kosmotropic salt may facilitate acidification of the fibroin protein solution. Accordingly, the first and second injection solutions may have a suitable pH. In one or more embodiments, the first injection solution including the chaotropic salt has a pH ranging from 3.0 to 9.5. For example, the first injection solution may have a pH ranging from a lower limit of one of 3.0, 3.5, 4.0, 4.5, 5.5, and 6.0 to an upper limit of one of 6.0, 6.5, 7.0, 7.5, 8.0, 8.5, 9.0, and 9.5, where any lower limit may be paired with any mathematically compatible upper limit. In one or more embodiments, the second injection solution including the kosmotropic salt has a pH ranging from 3.0 to 10.0. For example, the first injection solution may have a pH ranging from a lower limit of one of 3.0, 3.5, 4.0, 4.5, 5.0, 5.5, and 6.0, to an upper limit of one of 6.0, 6.5, 7.0, 7.5, 8.0, 8.5, 9.0, 9.5, and 10.0, where any lower limit may be paired with any mathematically compatible upper limit.

Then, the intermediate solution may be exposed to a shear force 207. In some embodiments, the shear force is applied as centrifugal force. In other embodiments, the shear force is applied by a chemical gradient line of a modified 3D printer, such as the 3D printer described herein. Suitable shear force that may be exerted on the intermediate solution may range from 300 to 700 MPa (megapascals). For example, the intermediate solution may be exposed to a shear force ranging from a lower limit of one of 300, 350, 400, 450, and 500 MPa to an upper limit of one of 500, 550, 600, 650, and 700 MPa, where any lower limit may be paired with any mathematically compatible upper limit. Upon exposure to the shear force, the structure of the fibroin protein in the intermediate solution may be altered such that the β-sheets self-align, providing a structure having stacks of β-sheets. Modification to the structure of the fibroin protein may provide a fibroin protein that has enhanced stability and increased crystallinity that can be manipulated to provide various fibroin protein products 209. Suitable fibroin protein products that may be produced according to method 200 include, but are not limited to, fibroin protein fibers, fibroin protein filaments, fibroin protein adhesives, fibroin protein films, fibroin protein foams, fibroin protein hydrogels, and fibroin protein nanofibrils.

3D Printed Fibroin Protein Products

As previously described, fibroin protein products may be produced by a 3-dimentionsal (3D) printer. Accordingly, another aspect of the present disclosure relates to a method and apparatus for 3D printing fibroin protein products. In particular, a 3D printer may be used to produce fibroin protein fibers and filaments. As used herein, "3d printing" (also referred to as additive manufacturing) refers to a process that builds a three-dimensional (3d) object from a 3d model data, such as from a computer-aided design (CAD) model. 3d printing is generally a layer-by-layer process in which a 3d object is built one layer at a time, and each successive layer is added to the previously constructed layer(s).

Figure 3:
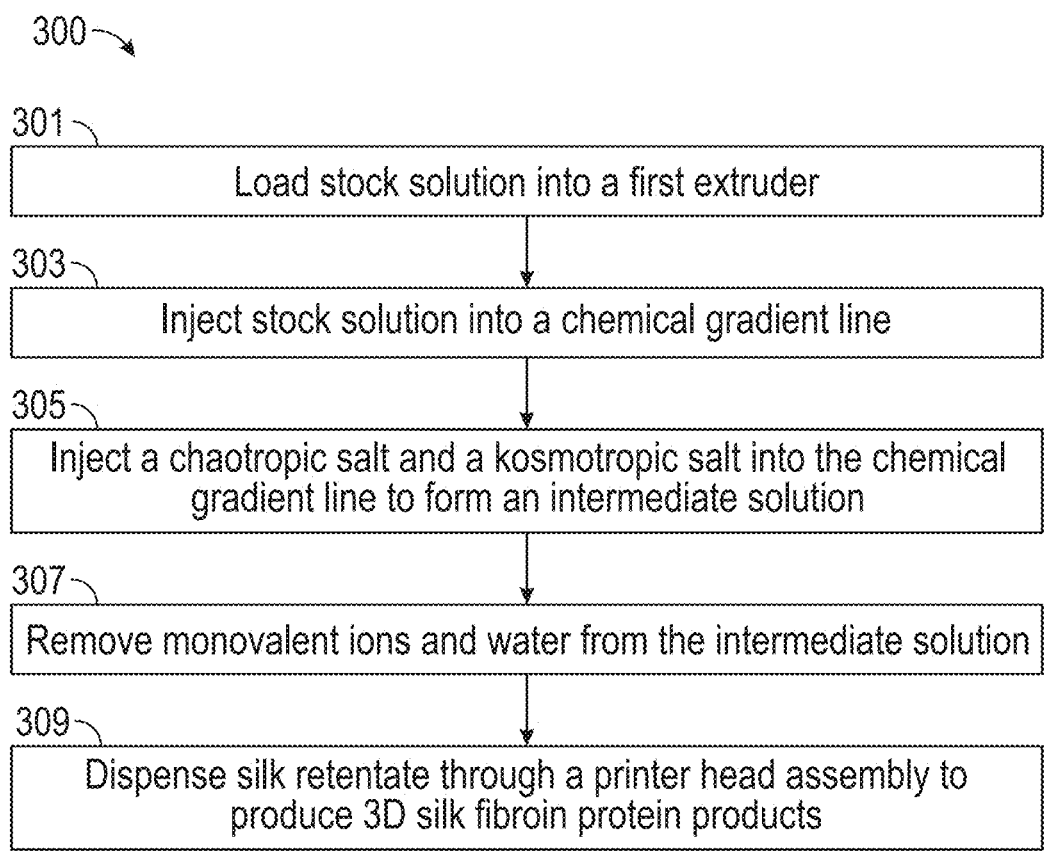
FIG. 3 is a block flow diagram of a method of producing a fibroin protein product in accordance with one or more embodiments of the present disclosure.
Figure 4A:
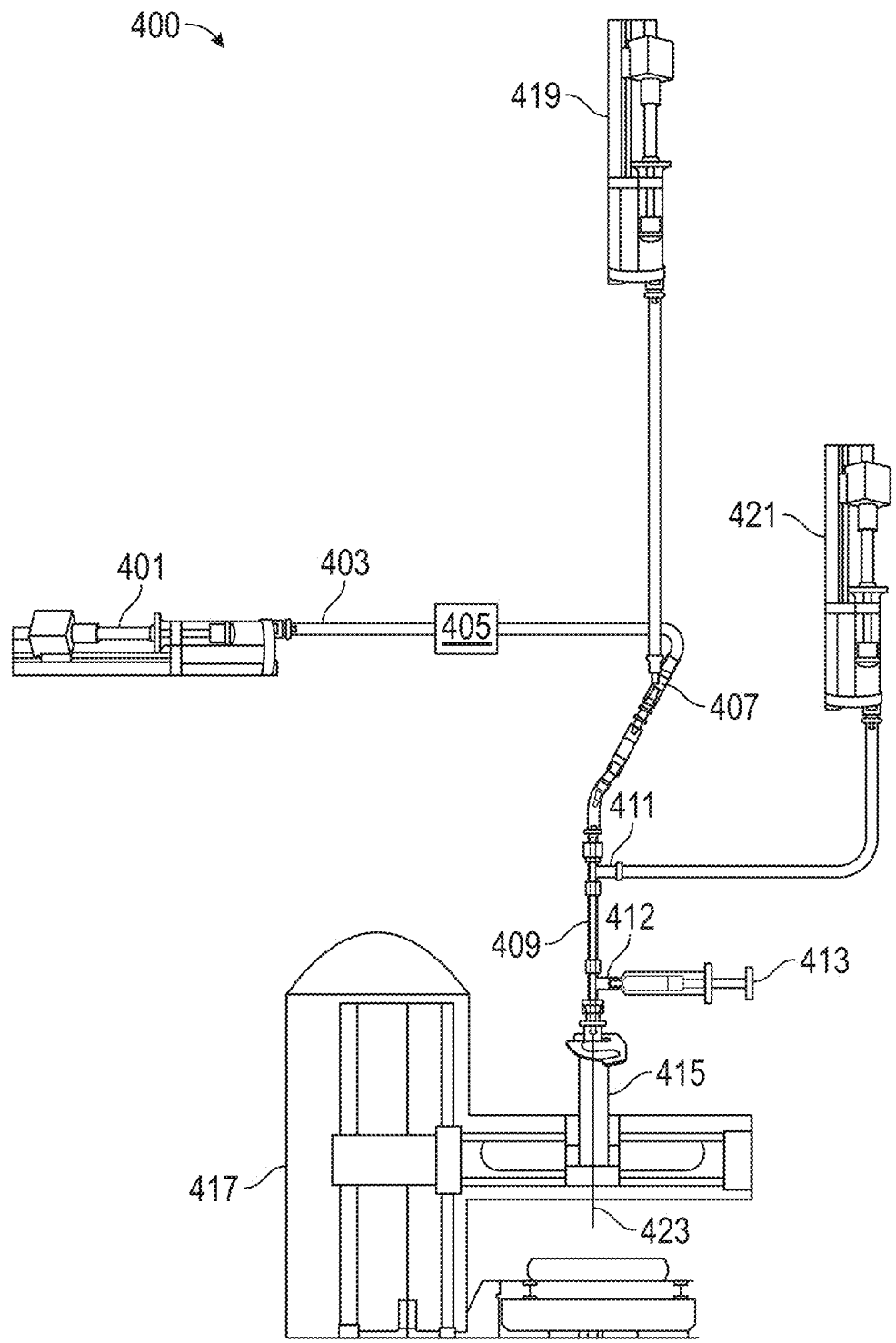
FIG. 4A is a diagram of a 3D printer in accordance with one or more embodiments of the present disclosure.

A method of producing fibroin protein products in accordance with one or more embodiments is shown in, and discussed with reference to, FIG. 3. In method 300, a stock solution including fibroin protein is loaded into a first extruder of a 3D printer 301. A diagram of an exemplary 3D printer is depicted in FIG. 4A. The stock solution may be a fibroin protein solution as previously described. The fibroin protein in the stock solution may have a structure that is largely amorphous, with a small amount of embedded β-sheets, as described above. Method 300 then includes injecting the stock solution into a chemical gradient line 303.

Figure 4B:
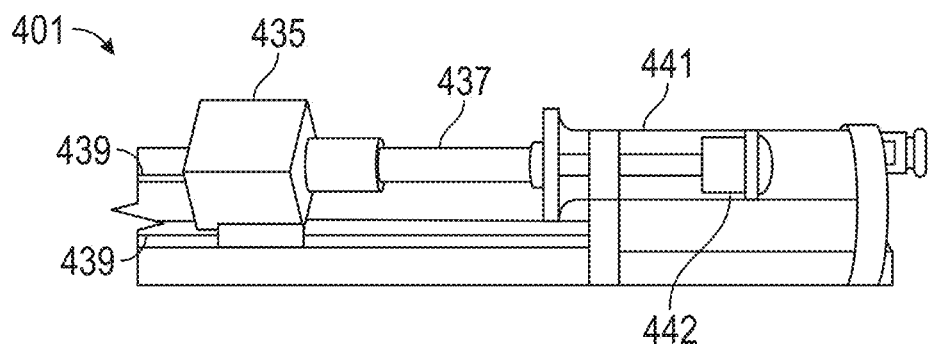
FIG. 4B is a diagram of an extruder in accordance with one or more embodiments of the present disclosure.

FIGS. 4A-E described herein show 3D printer arrangements in accordance with one or more embodiments of the present disclosure. As shown in FIG. 4A, 3D printer 400 includes first extruder 401 coupled to chemical gradient line 403. The details of first extruder 401 are shown in FIG. 4B. As shown in FIG. 4B, first extruder 401 includes a syringe housing 441 secured to parallel rods 439, a plunger housing secured to a linearly actuated carriage and a threaded rod 437 coupled to a fixed step motor 435 on a first end and freely rotating on a second end. In one or more embodiments, the threaded rod 437 is linearly aligned with the plunger housing and axially fixed to the linear actuated carriage and the linearly actuated carriage is configured to slide along parallel rods 439 and provide hydraulic pressure to drive translation of a plunger 442 into the syringe housing 441. The step motor of the first extruder may be configured to receive power and data from a microprocessing system included in printer body 417 (shown in FIG. 4A).

Figure 4C:
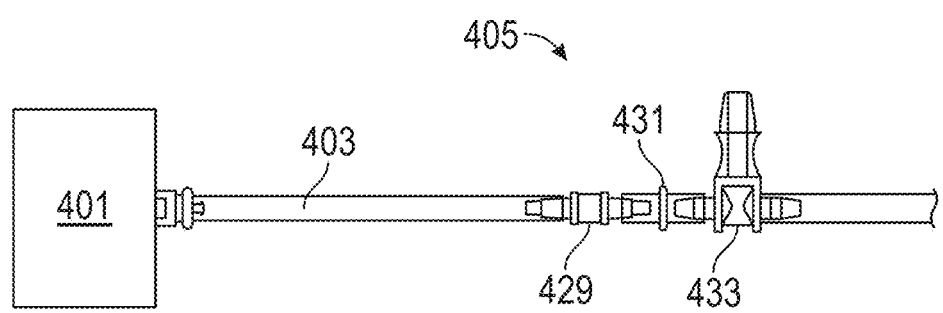
FIG. 4C is a diagram of a closed duct assembly in accordance with one or more embodiments of the present disclosure.

Chemical gradient line 403 may be any suitable line commonly used in 3D printing applications. In one or more embodiments, chemical gradient line 403 provides shear stress on the stock solution as it travels through the line. Shear stress from the chemical gradient line may be sufficient to induce self-alignment of the β-sheets in the fibroin protein, resulting in fibroin protein with an increased degree of crystallinity that may be printed as any of the aforementioned fibroin protein products. In one or more embodiments, the chemical gradient line is an IV line. Closed duct assembly 405 is coupled to chemical gradient line 403 downstream of first extruder 401. In some embodiments, the diameter of the chemical gradient line upstream of closed duct assembly 405 may be greater than the diameter of the chemical gradient line downstream of closed duct assembly 405 (details of the closed duct assembly not shown in FIG. 4A). In other embodiments, the diameter of the chemical gradient line is the same upstream and downstream of closed duct assembly 405. Closed duct assembly 405 may include various components that facilitate a pressure decrease within the chemical gradient line. As shown in FIG. 4C, closed duct assembly 405 may include a stepped barbed piece 429, a straight connecter 431, and a T-connecter 433. T-connecter 433 may be located at a high point of the chemical gradient to evacuate any air bubbles that may be present in the chemical gradient line once the stock solution has been injected.

Figure 4D:
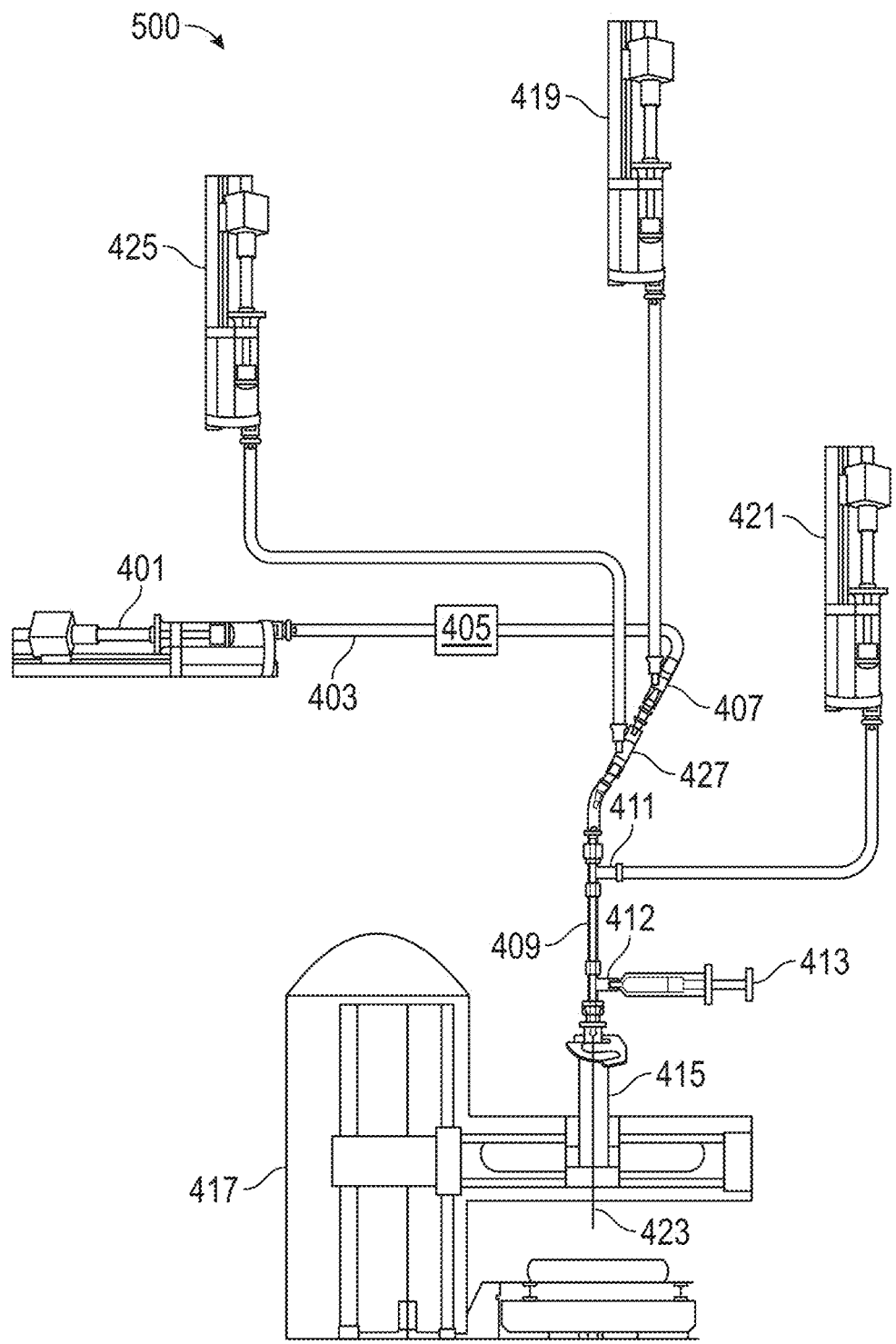
FIG. 4D is a diagram of a 3D printer in accordance with one or more embodiments of the present disclosure.

Once the stock solution is injected into the chemical gradient line, it may travel through closed duct assembly 405. Further downstream, at first injection site 407, an injection solution including a chaotropic salt or a kosmotropic salt may be injected, via second extruder 419, into the chemical gradient line such that the injected ions mix with the stock solution 305 to provide an intermediate solution. In one or more embodiments, a first injection solution including a chaotropic salt is injected into the chemical gradient line at a first injection site via a second extruder, and a second injection solution including a kosmotropic salt is injected at a second injection site, via a third extruder. A 3D printer 500 in accordance with such embodiments is shown in FIG. 4D, and includes second injection site 427 and third extruder 425. In other embodiments, a first injection solution including a kosmotropic ion is injected into the chemical gradient line, and there is no second injection solution. The chaotropic salt and the kosmotropic salt may be injected into the chemical gradient line in an amount such that the concentration of each salt in the intermediate solution corresponds to the concentration of the same in a native silk-producing gland, as described above.

Depending on the salt used, the injection solution may be acidic or basic. In one or more embodiments, the injection solution is an acidic solution including one or more salts described above. The injection solution may have a pH ranging from about 3.0 to about 9.5. For example, in one or more embodiments, the injection solution has a pH ranging from a lower limit of one of 3.0, 3.5, 4.0, 4.5, 5.0, 5.5, and 6.0 to an upper limit of one of 6.5, 7.0, 7.5, 8.0, 8.5, 9.0, and 9.5, where any lower limit may be paired with any mathematically compatible upper limit. In one or more particular embodiments, the injection solution has a pH ranging from 3.0 to 6.5.

After injecting the injection solutions including a chaotropic salt and a kosmotropic salt into the chemical gradient line, method 300 includes removing monovalent ions and water from the intermediate solution 307. Accordingly, in one or more embodiments the intermediate solution is passed through filter assembly 409 to remove monovalent ions and water. In particular, the filter assembly may selectively remove water and monovalent ions such as $Na^+$ and $Cl^-$, while divalent ions such as $HPO_4^{2-}$ and $SO_4^{2-}$ are left in solution. The filter assembly may be a hollow fiber filter. Suitable hollow fiber filters include any dialysis filters known in the art such as, for example, MicroKros ultrafiltration systems. In particular embodiments, the filter assembly is an SP-10 kD MicroKros® ultrafiltration system. The filter assembly may have an injection port 411 and a collection port 412 as shown in FIG. 4A. In some embodiments, the collection port may drain directly into a sink or other waste container. In other embodiments, the collection port may collect residual salt and water from the intermediate solution in collection syringe 413. In one or more embodiments, a purifying solution is injected into the injection port via a fourth extruder 421 to facilitate the removal of salt and water from the stock solution. The purifying solution may include an aqueous-based fluid, which may be the same as the aqueous-based fluid included in the stock solution. The purifying solution may include an additional polar solvent such as methanol, ethanol, propanol, isopropanol, butanol, ethylene glycol, and combinations thereof. In one or more particular embodiments, the purifying solution includes isopropanol.

In embodiments in which a purifying solution is injected into the filter assembly, the purifying solution may be injected into the intermediate solution continuously until the total amount of monovalent ions has sufficiently decreased and the intermediate solution is dehydrated. The purifying solution may be injected continuously so as to maintain a laminar flow.

Figure 4E:
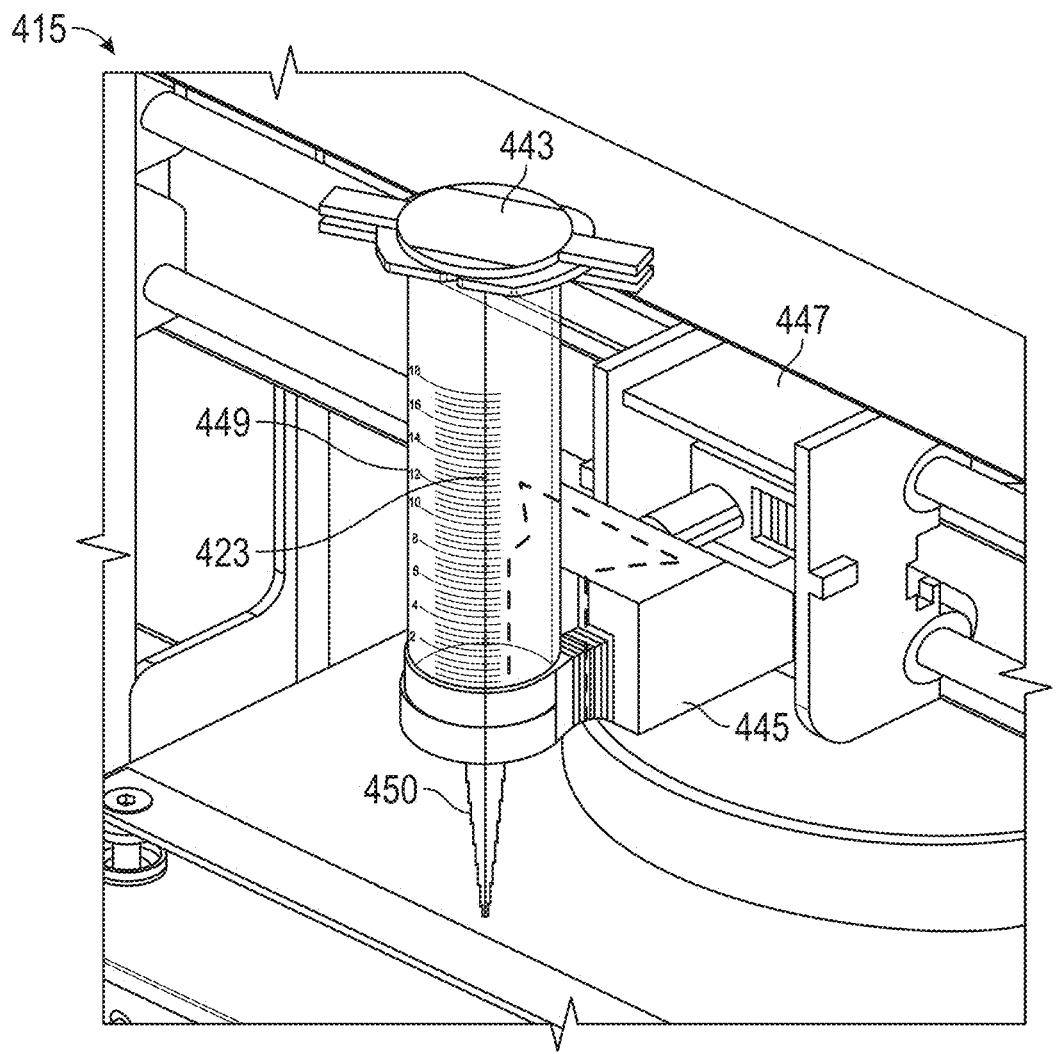
FIG. 4E is a diagram of a printer head assembly in accordance with one or more embodiments of the present disclosure.

Desalting and dehydrating of the stock solution may provide a printable silk retentate. In method 300, the dehydrated silk retentate is dispensed through printer head assembly 415 on printer body 417 to produce 3D fibroin protein products 309. A diagram of printer head assembly 415 is shown in FIG. 4E. Printer head assembly 415 includes x-axis carriage 447, slotted extension 445, syringe 449 in a syringe mount, optionally secured with a U-shaped bracket, glass capillary tube 423 suspended within the syringe by a flexible silicone mold, and syringe needle 450. Slotted extension 445 is coupled to x-axis carriage and is configured such that syringe 449 is easily replaceable. The chemical gradient line is fluidly connected to glass capillary tube 423 via cap 443 on the syringe. Capillary tube 423 runs through syringe 449 into syringe needle 450 to dispense the silk retentate and print fibroin protein products. Fibroin protein products printed via such method may have a smaller diameter as compared to fibroin protein products printed with the same printer head assembly excluding the capillary tube. The motion of syringe needle 450 may be controlled by a microprocessor included in printer body 417. In one or more embodiments, the microprocessor controls the 3-dimensional motion (i.e., the motion about the x-axis, y-axis, and z-axis) of the syringe needle, effectively producing a 3D printed fibroin protein product.

In one or more embodiments, syringe needle 450 includes a brush-like nozzle. A brush-like nozzle may be included in a syringe needle to increase shearing forces on the silk retentate to provide a fibroin protein product having the desired final protein structure. In one or more embodiments, a decreasing pressure gradient may be applied to the chemical gradient line of the 3D printer to augment the shearing forces, and facilitate the self-alignment of β-sheets in the fibroin protein.

Figure 5A:
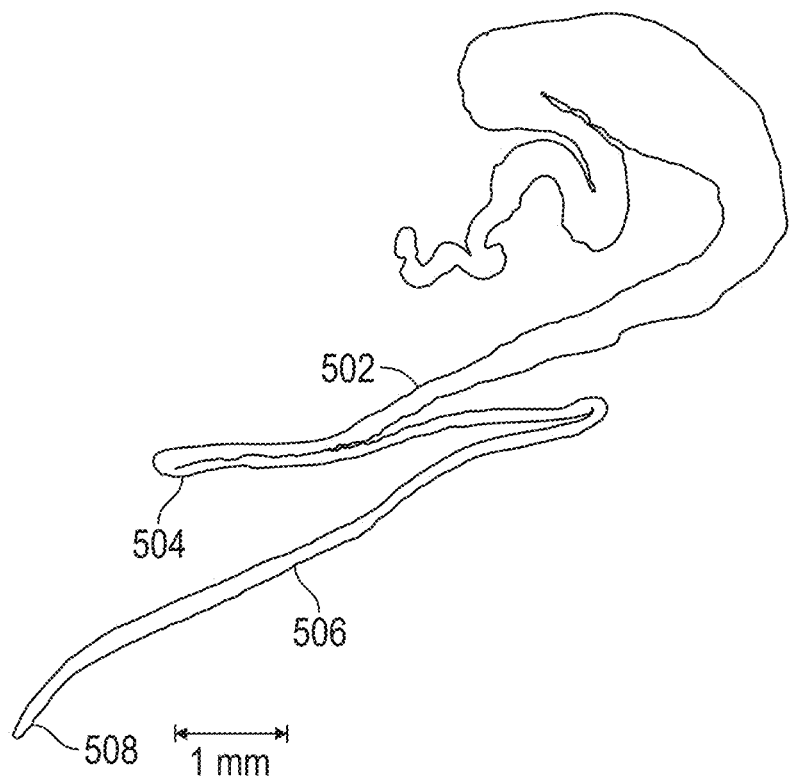
FIG. 5A is a diagram of a native gland of a *Nephila clavipes* in accordance with one or more embodiments of the present disclosure.

In one or more embodiments, parts of the 3D printer 400 are configured to correspond to a native silk-producing gland of an insect. In particular, the lengths of chemical gradient line 403, filter assembly 409 and capillary tube 423 may be scaled according to the lengths of "limbs" of a native silk-producing gland. FIG. 5A shows a diagram of a native silk-producing gland of a *Nephila clavipes* spider. As shown in FIG. 5A, the native gland includes Limb 1 502, Limb 2 504, Limb 3 506, and Spigot 508. In particular embodiments, the 3D printer is configured such that the chemical gradient line running from the first extruder to the filter assembly corresponds to Limb 1 502 in terms of relative length, the filter assembly corresponds to Limbs 2 504 and 3 506 in terms of relative length, and the capillary tube corresponds to the relative length of the Spigot 508. In other particular embodiments, the same components of a 3D printer in accordance with the present disclosure may correspond to limbs and spigots of a native silk-producing gland of another silk-producing insect, such as, but not limited to, a silkworm.

Figure 5B:
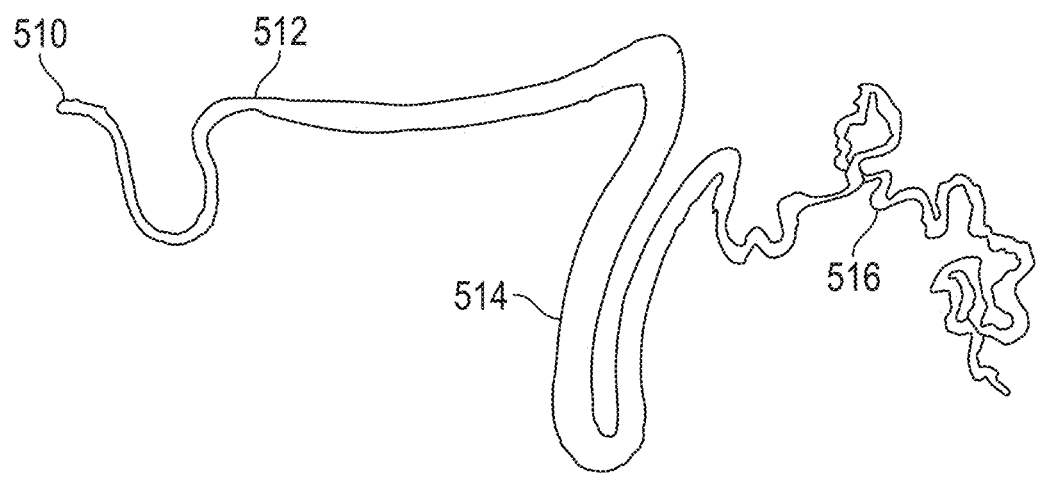
FIG. 5B is a diagram of a native gland of a *Bombyx mori* in accordance with one or more embodiments of the present disclosure.

For example, FIG. 5B shows a diagram of a native silk-producing gland of a *Bombyx mori* silkworm. As shown in FIG. 5B, the *Bombyx mori* silk-producing glans includes posterior silk gland 516, middle silk gland 514, funnel 512, and anterior silk gland 510. Embodiments in which the 3D printer is configured to correspond to the native-silk producing gland of a *Bombyx mori* may have a length of the chemical gradient line running from the first extruder to the filter assembly that corresponds to the length of posterior silk gland 516, a length of the filter assembly that corresponds to the length of middle silk gland 514 and funnel 512, and a length of the capillary tube that corresponds to the length of anterior silk gland 510.

Accordingly, in one or more embodiments a ratio of a length of the chemical gradient line running from the first extruder to the filter assembly to a length of the filter assembly to a length of the capillary tube may range from 1:1.5:0.1 to 1:2:0.2. In one or more particular embodiments, the ratio is 1:1.8:0.12.

In one or more embodiments, printer body 417 includes a microprocessor. The microprocessor may provide control of the travel speed of the x/y/z (3D) axis of printing. The microprocessor may be also connected to the first extruder of the 3D printer, thus providing control of the rate of extrusion of a fibroin protein stock solution from first extruder 401. Any microprocessor known in the art may be included in the printer body. In one or more particular embodiments, the microprocessor is an Arduino microprocessor.

As described above, 3D printed fibroin protein products may include fibroin protein fibers and filaments. 3D printed fibroin protein fibers and filaments may be utilized in various applications, such as biomedical applications. For example, using 3D printing method 300, biomaterials such as ligaments, tendons, muscle fibers, scaffolds, and grafts may all be produced from fibroin protein. The potential to produce the above biomaterials using compositions and methods disclosed herein may reduce costs and increase patient outcomes in the medical field.

EXAMPLES

The following examples are illustrative of the compositions and methods described above. They are not meant to limit the scope of the disclosure.

Figure 6A:
FIG. 6A is a photograph of an exemplary fibroin protein product in accordance with one or more embodiments of the present disclosure.
Figure 6B:
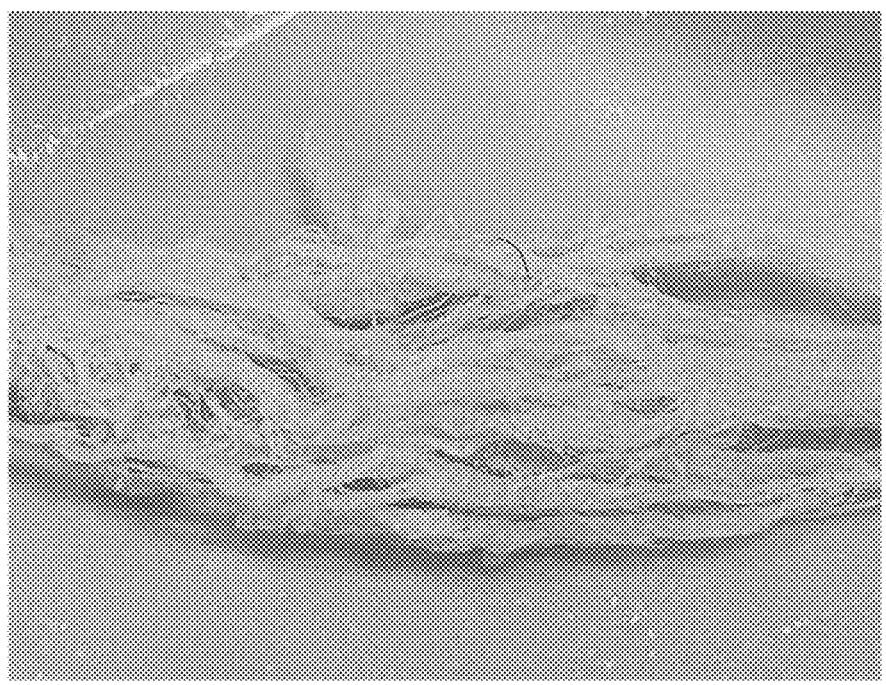
FIG. 6B is a photograph of an exemplary fibroin protein product in accordance with one or more embodiments of the present disclosure.

FIGS. 6A and 6B show exemplary fibroin protein products prepared according to methods described herein. FIG. 6A is a photograph of a fibroin protein adhesive. FIG. 6B is a photograph of fibroin protein fibers.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method of producing a fibroin protein product comprising:
   providing a stock solution of fibroin protein;
   injecting the stock solution into a chemical gradient line of a 3D printer;
   injecting a first injection solution comprising a chaotropic salt into the stock solution via at least one injection site on the chemical gradient line;
   injecting a second injection solution comprising a kosmotropic salt into the stock solution via the at least one injection site on the chemical gradient line to provide an intermediate solution; and
   exposing the intermediate solution to a shear force thereby producing the fibroin protein product.

2. The method of claim 1, further comprising:
   after injecting the first injection solution and the second injection solution into the stock solution to provide the intermediate solution, passing the intermediate solution through a filter thereby removing monovalent ions and water from the intermediate solution to provide a dehydrated silk retentate.

3. The method of claim 2, further comprising:
   after passing the intermediate solution through the filter, dispensing the dehydrated silk retentate through a printer head assembly, wherein an x-axis motion, a y-axis motion, and a z-axis motion of the dispensing are controlled by a microprocessor of the 3D printer such that a 3D silk fibroin protein product is produced.

4. The method of claim 1, wherein the shear force is in a range from 300 to 700 MPa.

5. The method of claim 1, wherein the first injection solution and the second injection solution have a pH ranging from 3.0 to 9.5.

6. The method of claim 1, wherein the stock solution has a pH ranging from 4.0 to 12.0.

7. The method of claim 1, wherein the fibroin protein product is selected from the group consisting of a fiber, a filament, an adhesive, a hydrogel, a nanofibril, a film, a foam, and combinations thereof.

* * * * *